United States Patent [19]

Hall et al.

[11] 4,021,488

[45] May 3, 1977

[54] 1-ACETYL-3,3-DIMETHYL-(2-PROPENYL)-CYCLOHEXANE

[75] Inventors: John B. Hall, Rumson; Mark A. Sprecker, Sea Bright; Frederick Louis Schmitt, Holmdel; Manfred Hugo Vock, Locust, all of N.J.

[73] Assignee: International Flavors & Fragrances Inc., New York, N.Y.

[22] Filed: Aug. 11, 1976

[21] Appl. No.: 713,429

[52] U.S. Cl. .................. 260/586 R; 252/89 R; 252/108; 252/173; 252/368; 260/586 C; 424/48; 424/52; 424/69; 426/534; 426/538; 426/648

[51] Int. Cl.² .............................. C07C 49/61

[58] Field of Search .................. 260/586 R

[56] References Cited

UNITED STATES PATENTS 3,875,241   4/1975   Corber et al. .............. 260/586 R
3,929,895   12/1975   Hall .............................. 260/586 R

*Primary Examiner*—Norman Morgenstern
*Attorney, Agent, or Firm*—Arthur L. Liberman; Franklin D. Wolffe

[57] ABSTRACT

Described is the compound 1-acetyl-3,3-dimethyl-(2-propenyl)cyclohexane, a process for preparing same by means of reacting an allylic halide with acetyl-3,3-dimethylcyclohexane using a phase transfer agent and in a two phase system according to the reaction:

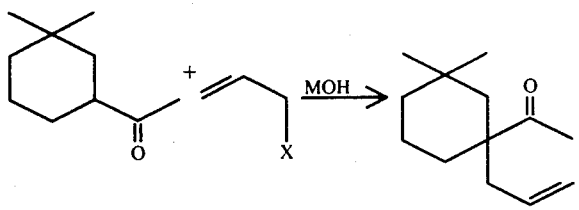

wherein X is chloro or bromo, processes for adding 1-acetyl-3,3-dimethyl-(2-propenyl)cyclohexane to consumable materials whereby:
  i. In foodstuffs and medicinal products, fruity, pineapple, allyl-caproate-like, galbanum and woody aroma characteristics are augmented or enhanced and rosey, ionone, oriental-like and woody flavor characteristics are augmented or enhanced; and
  ii. In perfumes and perfumed articles, sweet, earthy, animal aromas with pineapple and ambery nuances and tobacco/animal notes are imparted, augmented and/or enhanced and flavor compositions and perfume compositions containing 1-acetyl-3,3-dimethyl-(2-propenyl)cyclohexane.

1 Claim, 5 Drawing Figures

FIG.1
EXAMPLE I

NMR SPECTRUM FOR
(1,1-DIMETHYL-3-ACETYL-3(2-PROPENYL)CYCLOHEXANE

SOLVENT (CDCl₃)
SWEEP WIDTH 2000 Hz.

IR SPECTRUM FOR
(1,1-DIMETHYL-3-ACETYL-3(2-PROPENYL)CYCLOHEXANE

FIG.2
EXAMPLE I

FIG. 3
NMR SPECTRUM EXAMPLE I 1,1-DIMETHYL-3(4-PENTENOYL)CYCLOHEXANE
SOLVENT: CDCl$_3$
SWEEP WIDTH: 2000 Hz.

NMR SPECTRUM FOR:

SOLVENT: CDCl$_3$
SWEEP WIDTH: 2000 Hz.

FIG. 4
EXAMPLE I

FIG.5
EXAMPLE I

1-ACETYL-3,3-DIMETHYL-(2-PROPENYL)CYCLOHEXANE

BACKGROUND OF THE INVENTION

The present invention provides the compound 1-acetyl-3,3-dimethyl-(2-propenyl)cyclohexane and a straight forward, economical process directed towards synthesizing 1-acetyl-3,3-dimethyl-(2-propenyl)cyclohexane by reaction of an allylic halide with acetyl-3,3-dimethylcyclohexane, and utilization of 1-acetyl-3,3-dimethyl-(2-propenyl)cyclohexane for its organoleptic properties in perfumes, perfumed articles, foodstuffs and medicinal products.

In the perfumery art there is a considerable need for substituents having woody, earthy, sweet, animal aroma characteristics with pineapple/amber nuances and in addition, tobacco/animal aromas. Specifically described are materials having such an economical profile but which do not discolor with age. Such fragrance materials have a wide utilization in the presence of these perfume compounds. A minimum amount of such materials that give rise to these properties is available from natural sources but the natural materials are subject to wide variations in quality, are expensive, and are limited or often in critically short supply.

There is a continuing search for compositions which can vary, fortify, modify, enhance, augment or otherwise improve the flavor and aroma of foodstuffs and medicinal products. To be satisfactory, such compositions should be stable, non-toxic and blendable with other ingredients to provide its own unique flavor and aroma nuance without detracting from the co-ingredients. Preferably, such compositions should be naturally occurring or present in natural foodstuffs so that its ingestible safety can be readily recognized. These materials should be capable of being synthesized in a simple and economical manner. The need for safe flavors in the fruity flavor area, e.g. pineapple, raspberry and other berry-fruit is well-known particularly in the ice cream and yogurt flavor areas and in the cold beverage area. More specifically, there is a need for the development of non-toxic materials which can replace natural materials not readily available, having fruity, pineapple, galbanum and woody aroma characteristics with rosey, ionone-like, oriental and woody flavor characteristics.

Firmenich's Dutch published application 7,500,838 discloses the preparation of the compound having the structure:

and discloses its use in perfumery and in augmenting foodstuff flavors. The perfumery use of this compound and other members of its class as "floral, green, herbaceous and chypre" useful in galbanum resinoids is also disclosed.

The compounds disclosed in Dutch published application 7,500,838 have organoleptic properties which causes them to be different in kind from 1-acetyl-3,3-dimethyl-(2-propenyl)cyclohexane, which has unobvious, unexpected and advantageous characteristics in the field of augmenting or enhancing the organoleptic impressions of foodstuffs, foodstuff flavors, perfumes, perfumed articles and medicinal products.

Insofar as relevant prior art concerning the process for preparing 1-acetyl-3,3-dimethyl-(2-propenyl)cyclohexane, German Pat. No. 1,244,784, issued on July 20, 1967, discloses the reaction:

wherein R can be one of alkyl, alkenyl, allyl, propargyl, cyclohexyl or benzyl; X is chloro or bromo and $R_1$, $R_2$, $R_3$, $R_4$ and $R_5$ can be hydrogen, alkyl, alkenyl or phenyl. The reaction of the German Patent is limited to ketones. Although such ketones could be unsaturated, the nature of the reaction is different in kind from the reaction of the instant invention.

BRIEF DESCRIPTION OF THE DRAWINGS

FIG. 3 represents the NMR spectrum for the compound having the structure:

produced according to Example I.

FIG. 4 represents the NMR spectrum for the compound having the structure:

(structure represents "cis" and/or "trans" isomer or both isomers)

FIG. 5 represents the Infrared spectrum for the compound having the structure:

(structure represents "cis" and/or "trans" isomer or both isomers)

The present invention relates to the novel compound, 1-acetyl-3,3-dimethyl-(2-propenyl)cyclohexane having the structure:

a process for producing same and perfumes, perfumed articles, foodstuffs, foodstuff flavorings and medicinal products containing 1-acetyl-3,3-dimethyl-(2-propenyl)cyclohexane.

The compound 1-acetyl-3,3-dimethyl-(2-propenyl)-cyclohexane is capable of augmenting or enhancing pineapple, raspberry and berry-fruit flavors by providing thereto fruity, pineapple, allyl caproate-like, galbanum and woody aroma characteristics along with rosey, ionone, oriental and woody flavor characteristics.

The compound 1-acetyl-3,3-dimethyl-(2-propenyl)-cyclohexane is also capable of modifying or enhancing the aroma characteristics of perfumed compositions and perfumed articles by imparting thereto woody, earthy, amber-like, sweet, animal, tobacco/animal notes with pineapple/amber nuances, thus fulfilling a need in the field of perfumery.

The compound 1-acetyl-3,3-dimethyl-(2-propenyl)-cyclohexane is produced by reacting acetyl-3,3-dimethylcyclohexane with an allyl halide in the presence of an inert solvent, and an alkali metal hydroxide and in the presence of a "phase transfer agent". The reaction is carried out in a two phase system. Thus, one aspect of our invention is illustrated in the following reaction:

wherein X is chloro or bromo and wherein M is alkali metal.

One aspect of our invention involves the aforementioned process comprising the step of placing the reactants for the process and the base, respectively, in two immiscible phases; an organic phase and either (i) an aqueous base phase or (ii) a solid base phase with the reactants being located substantially entirely in the first mentioned organic phase and the base being located substantially entirely in the second mentioned phase; and adding to this two phase system a "phase transfer agent" which may be one or more of several organic quaternary ammonium salts.

Specific examples of phase transfer agents useful in our invention are as follows:

Tricapryl methyl ammonium chloride;
Cetyl trimethyl ammonium chloride;
Cetyl trimethyl ammonium bromide; and
Benzyl trimethyl ammonium hydroxide.

In general, the phase transfer agents most preferred have the generic formula:

wherein at least one of $R_1$, $R_2$, $R_3$ and $R_4$ is $C_6$–$C_{14}$ aryl, $C_6$–$C_{10}$ aralkyl, $C_6$–$C_{20}$ alkyl, $C_6$–$C_{14}$ alkaryl and $C_6$–$C_{20}$ alkenyl and the other of $R_2$, $R_3$ and $R_4$ is alkyl such as methyl, ethyl, n-propyl, i-propyl, 1-butyl, 2-butyl, 1-methyl-2-propyl, 1-pentyl and 1-octyl and $Z^-$ is an anion such as chloride, bromide and hydroxide.

The process of our invention is carried out in an inexpensive solvent which is inert to the reaction system such as toluene, benzene, o-xylene, m-xylene, p-xylene, ethyl benzene, n-hexane, cyclohexane, methylene chloride and o-dichlorobenzene.

The process of our invention is carried out at a temperature in the range of from about 10° C up to about 150° C with a temperature range of 50°–120° C being preferred. The reaction time is inversely proportional to the reaction temperature, with lower reaction temperatures giving rise to greater reaction times; and, accordingly, the reaction time ranges from about 30 minutes up to about 10 hours.

In the reaction of our invention the mole ratio of 1-acetyl-3,3-dimethylcyclohexane to allyl halide reactant is in the range of from 0.5:1.5 up to about 1.5:0.5 with a preferred ratio being from about 1:1 up to about 1:1.2.

The mole ratio of base to allylic halide in the reaction mass may be in the range of from about 0.75:1 up to about 1.5:1 with a preferred ratio of base:allylic halide being from about 1:1 up to about 1.2:1.

The quantity of "phase transfer agent" in the reaction mass, based on the amount of 1-acetyl-3,3-dimethylcyclohexane in the reaction mass, may vary from 0.5 grams per mole of 1-acetyl-3,3-dimethylcyclohexane up to 25 grams per mole, with a preferred concentration of phase transfer agent being in the range of from about 2.5 up to about 7.5 grams of phase transfer agent per mole of 1-acetyl-3,3-dimethylcyclohexane.

The reaction of our invention is preferably carried out at atmospheric pressure since that is the most convenient condition, however, lower or higher pressures can be used without detrimentally affecting the ultimate yield of desired reaction product.

The particular base used in the reaction is critical and, preferred are, sodium hydroxide and potassium hydroxide.

When the compound 1-acetyl-3,3-dimethyl-(2-propenyl)cyclohexane of our invention is used as a food flavor adjuvant, the nature of the co-ingredients included with the compound 1-acetyl-3,3-dimethyl-(2-propenyl)cyclohexane in formulating the product composition will also serve to alter, modify, augment or enhance the organoleptic characteristics of the ultimate foodstuff treated therewith.

As used herein in regard to flavors, the terms alter, modify and augment in their various form means "supplying or imparting flavor character or note to otherwise bland, relatively tasteless substances or augmenting the existing flavor characteristic where a natural flavor is deficient in some regard or supplementing the existing flavor impression to modify its quality, character or taste. "

The term enhance is used herein to mean the intensification of a flavor or aroma characteristic or note without the modification of the quality thereof. Thus, "enhancement" of a flavor or aroma means that the enhancement agent does not add any additional flavor note.

As used herein, the term foodstuff includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term medicinal product includes both solids and liquids which are ingestible non-toxic materials which have medicinal value such as cough syrups, cough drops, aspirin and chewable medicinal tablets.

The term chewing gum is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the compound 1-acetyl-3,3-dimethyl(2-propenyl)cyclohexane of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly " acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and acetals (e.g., 1,1-diethoxy-ethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the compound 1-acetyl-3,3-dimethyl(2-propenyl)cyclohexane of our invention by not covering or spoiling the organoleptic properties (aroma and/or taste) thereof; (ii) be non-reactive with the compound 1-acetyl-3,3-dimethyl-(2-propenyl)cyclohexane of our invention and (iii) be capable of providing an environment in which the compound 1-acetyl-3,3-dimethyl-(2-propenyl)cyclohexane can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 1-acetyl-3,3-dimethyl-(2-propenyl)cyclohexane employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the compound 1-acetyl-3,3-dimethyl-(2-propenyl)cyclohexane will, of course, substantially vitiate any possibility of obtaining the desired results while excess quantities prove needlessly costly and in extreme cases, may disrupt the flavor-aroma balance, thus proving self-defeating. Accordingly, the terminology effective amount and sufficient amount is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the compound 1-acetyl-3,3-dimethyl-(2-propenyl)cyclohexane ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the compound 1-acetyl-3,3-dimethyl-(2-propenyl)cyclohexane is added to the foodstuff as an integral component of a flavoring composition, it is, of course, essential that the total quantity of flavoring composition employed be sufficient to yield an effective 1-acetyl-3,3-dimethyl-(2-propenyl)cyclohexane concentration in the foodstuff product.

Food flavoring compositions prepared in accordance with the present invention preferably contain the compound 1-acetyl-3,3-dimethyl-(2-propenyl)cyclohexane in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the compound 1-acetyl-3,3-dimethyl-(2-propenyl)cyclohexane with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the compound 1-acetyl-3,3-dimethyl-(2-propenyl)cyclohexane in a dry blender until the requisite degree of uniformity is achieved.

It is presently preferred to combine with the compound 1-acetyl-3,3-dimethyl-(2-propenyl)cyclohexane of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;

Guiacol;
Ethyl pelargonate;
Cinnamaldehyde;
Methyl anthranilate;
5-Methyl furfural;
isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal
2-Phenyl-2-hexenal;
2-Phenyl-2-pentenal;
3-Phenyl-4-pentenal diethyl acetal;
Damascone (1-crotonyl-2,2,6-trimethylcyclohex-1-one)
Damascenone (1-crotonyl-2,2,6-trimethylcyclohexa-1,5-diene)
Beta-cyclohomocitral (2,2,6-trimethyl-cyclohex-1-ene carboxaldehyde)
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene); and
2-(4-Hydroxy-4-methylpentyl) norbornadiene prepared according to U.S. Application for U.S. Patent 461,703, filed on Apr. 17, 1974.

The compound 1-acetyl-3,3-dimethyl-(2-propenyl)-cyclohexane and one or more auxiliary perfume ingredients, including, for example, alcohols, aldehydes, ketones, terpinic hydrocarbons, nitriles, esters, lactones, natural essential oils and synthetic essential oils, may be admixed so that the combined odors of the individual components produce a pleasant and desired fragrance, particularly and preferably in rose fragrances. Such perfume compositions usually contain (a) the main note or the bouquet or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, the compound 1-acetyl-3,3-dimethyl-(2-propenyl)cyclohexane can be used to alter, modify or enhance the aroma characteristics of a perfume composition, for example, by utilizing or moderating the olfactory reaction contributed by another ingredient in the composition.

The amount of 1-acetyl-3,3-dimethyl-(2-propenyl)-cyclohexane of our invention which will be effective in perfume compositions as well as in perfumed articles and colognes depends on many factors, including the other ingredients, their amounts and the effects which are desired. It has been found that perfume compositions containing as little as 0.01% of 1-acetyl-3,3-dimethyl-(2-propenyl)cyclohexane or even less (e.g., 0.005%) can be used to impart a woody, earthy, amber-like, earthy/ animal aroma with pineapple/amber nuances to soaps, cosmetics or other products. The amount employed can range up to 70% of the fragrance components and will depend on considerations of cost, nature of the end product, the effect desired on thd finished product and the particular fragrance sought.

The compound 1-acetyl-3,3-dimethyl-(2-propenyl)-cyclohexane of our invention is useful [taken alone or together with other ingredients in perfume compositions] as (an) olfactory components(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component (s) as little as 1% of 1-acetyl-3,3-dimethyl-(2-propenyl)cyclohexane will suffice to impart an intense floral note to rose formulations. Generally, no more than 3% of 1-acetyl-3,3-dimethyl-(2-propenyl) cyclohexane, based on the ultimate end product, is required in the perfume composition.

In addition, the perfume composition or fragrance composition of our invention can contain a vehicle, or carrier for the compound 1-acetyl-3,3-dimethyl-(2-propenyl) cyclohexane. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the compound 1-acetyl-3,3-dimethyl-(2-propenyl)cyclohexane of our invention can be utilized to alter, modify or enhance sensory properties, particularly organoleptic properties, such as flavor(s) and/or fragrance(s) of a wide variety of consumable materials.

The following examples serve to illustrate our invention and the invention is to be considered restricted thereto only as indicated in the appended claims.

All parts and percentages given herein are by weight unless otherwise specified.

EXAMPLE I

PREPARATION OF 1-ACETYL-3,3-DIMETHYL-(2-PROPENYL)CYCLOHEXANE (minor product)

Allyl chloride (222 grams, 3.8 moles) are added over a period of 15 minutes to a stirred slurry of 1-acetyl-3,3dimethylcyclohexane (462 grams, 3 moles), granular sodium hydroxide (180 grams, 4.5 moles), Aliquat 336 (tricapryl methyl ammonium chloride) (24 grams) and toluene (200 grams) at 70° C. The slurry is heated to reflux for 7.5 hours at the end of which period of time the temperature rises to 83° C. The slurry is then cooled and 1 liter of water is added to the reaction mass with stirring. The organic phase of the reaction mass is washed twice with water and distilled through a 12 × ½ inches packed Goodloe column fixed with an automatic reflux head set at a 19:1 reflux take-off ratio (85° C., 2.7 mm Hg pressure) yielding 275 grams of product having the structure:

(56% conversion), 40 grams of the compound having the structure:

(8% yield) and 147 grams of 1-acetyl-3,3-dimethylcyclohexane.

When using sodium hydride instead of sodium hydroxide a compound having the structure:

is produced.

Figure 1:
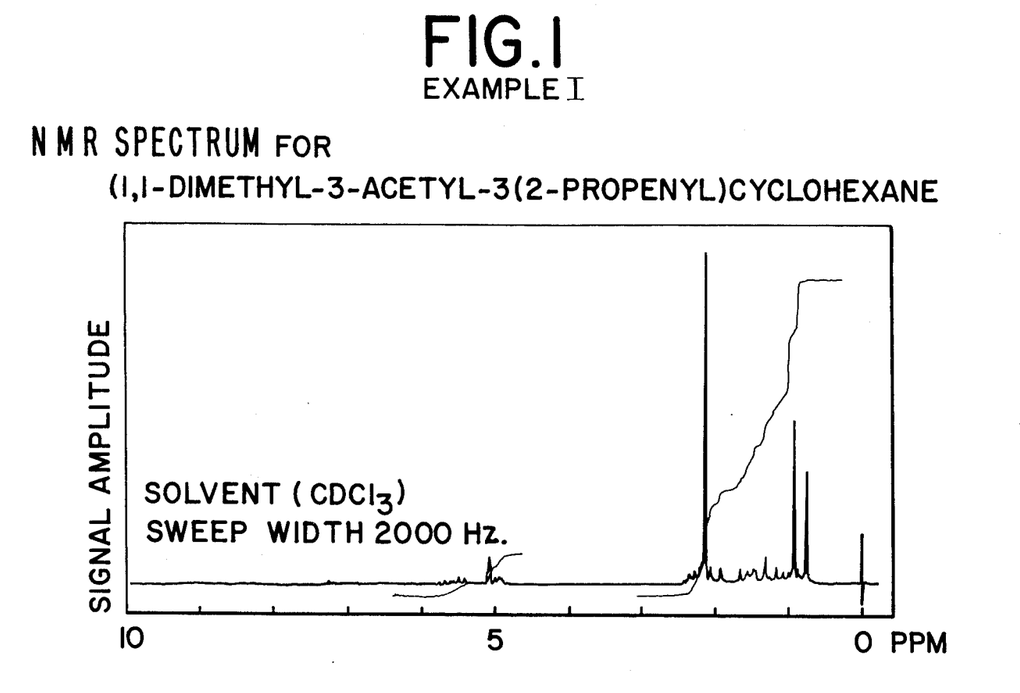
FIG. 1 represents the NMR spectrum for 1-acetyl-3,3-dimethyl-(2-propenyl)cyclohexane produced according to Example I.

The NMR spectrum for the compound having the structure:

is set forth in FIg. 1. The Infrared spectrum for this compound is set forth in FIG. 2.

The NMR analysis is as follows:

| δ, ppm | Interpretation |
|---|---|
| 0.74 (s, 3) | |
| 0.90 (s, 3) | methyl groups "A" |
| 2.14 (s, 3) | CH₃ Group "B" |
| 4.8⟶5.1 (m, 2) | CH₂ Group C |
| 5.4⟶5.8 (m, 1) | H_D |

Figure 2:
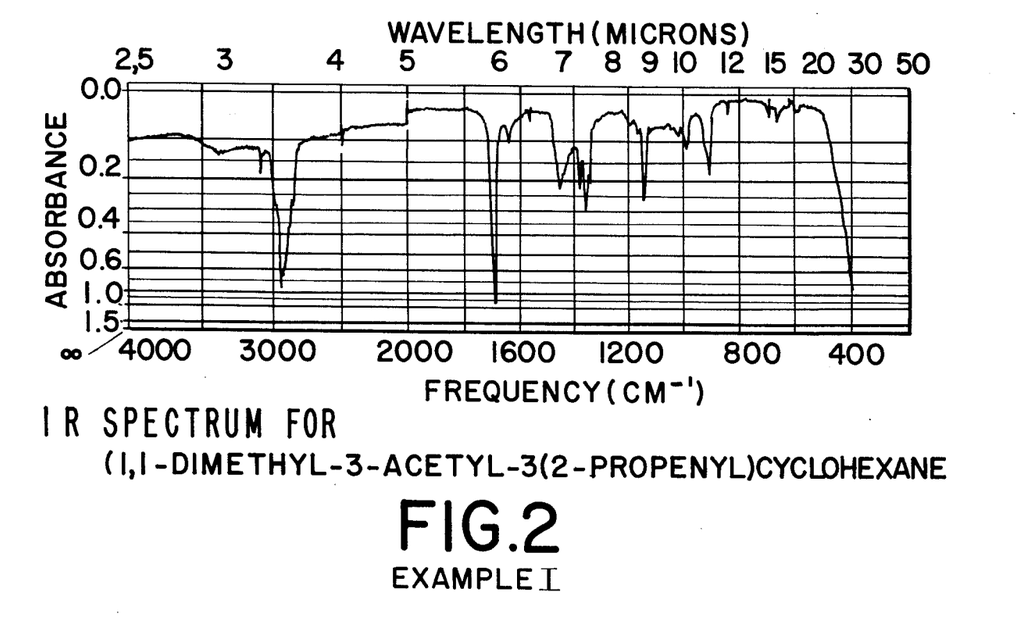
FIG. 2 represents the Infrared spectrum for 1-acetyl-3,3-dimethyl-(2-propenyl)cyclohexane produced according to Example I.

The Infrared analysis is as follows:

C=O, 1690 cm⁻¹:

C=C; 1660.

The Mass Spectral analysis is as follows: m/e= 95, 94, 69, 41, 109, 55, 194 (parent peak).

Figure 3:
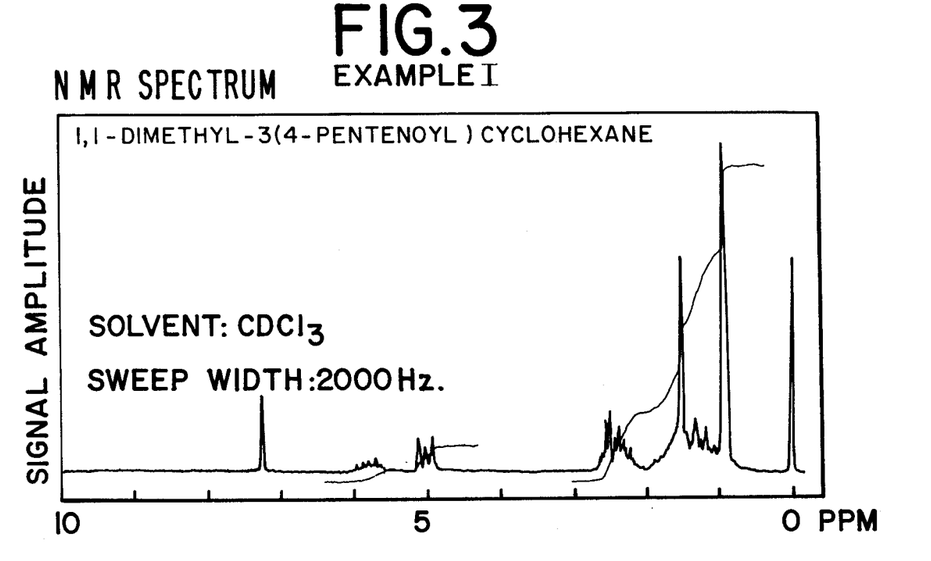

The NMR spectrum for the compound having the structure:

is set forth in FIG. 3. The NMR analysis is as follows:

| δ, ppm | Interpretation |
| --- | --- |
| 0.90 (s, 3) | Methyl Groups "A" |
| 0.93 (s, 3) | |
| 2.2→2.65 (m, 5) | CH$_2$'s "B" and H$_C$ |
| 4.60–5.12 (m, 2) | CH$_2$ "D" |
| 5.50–5.95 (m, 1) | H$_E$ |

The Mass Spectral analysis is as follows: m/e=69, 111, 55, 41, 83, 139, 194 (parent peak).

Figure 4:
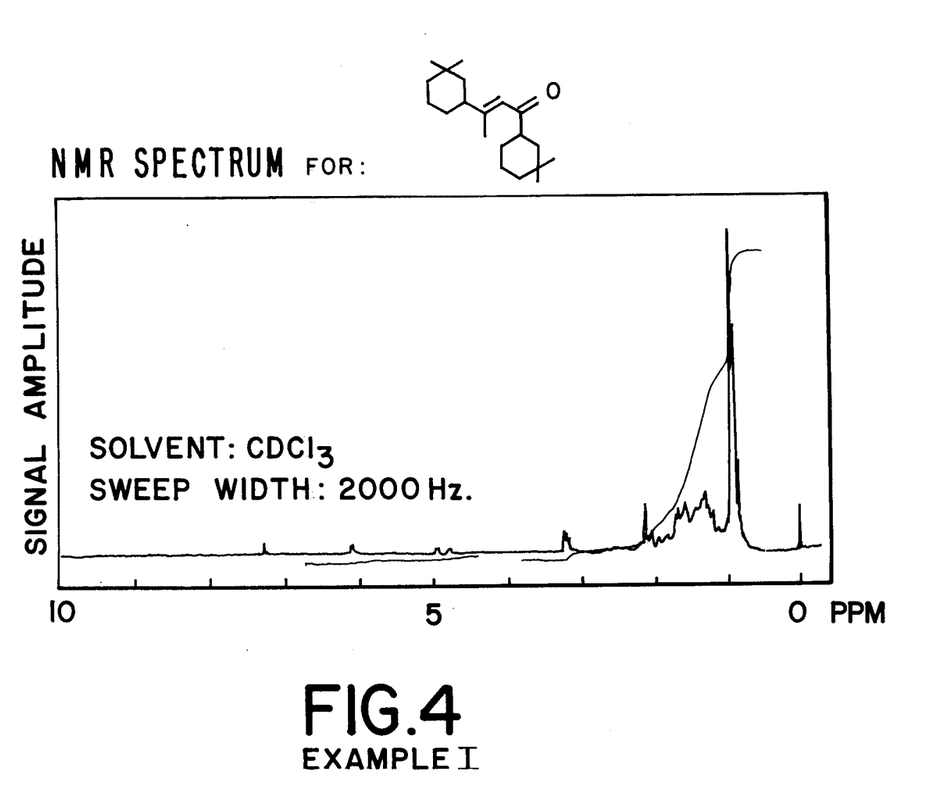

The NMR spectrum for the compound having the structure:

(stereochemistry unknown)

(produced when using sodium hydride) is set forth in FIG. 4. The Infrared spectrum is set forth in FIG. 5.

The NMR analysis is as follows:

(stereochemistry unknown)

| δ, ppm | Interpretation |
| --- | --- |
| 0.83–0.93 | Methyl Groups "A" |
| 2.08 (d, 1) small coupling | J=(Hz) CH$_3$ "B" |

(stereochemistry unknown)

| δ, ppm | Interpretation |
| --- | --- |
| scattered allylic H resonances | H$_D$ |

Figure 5:
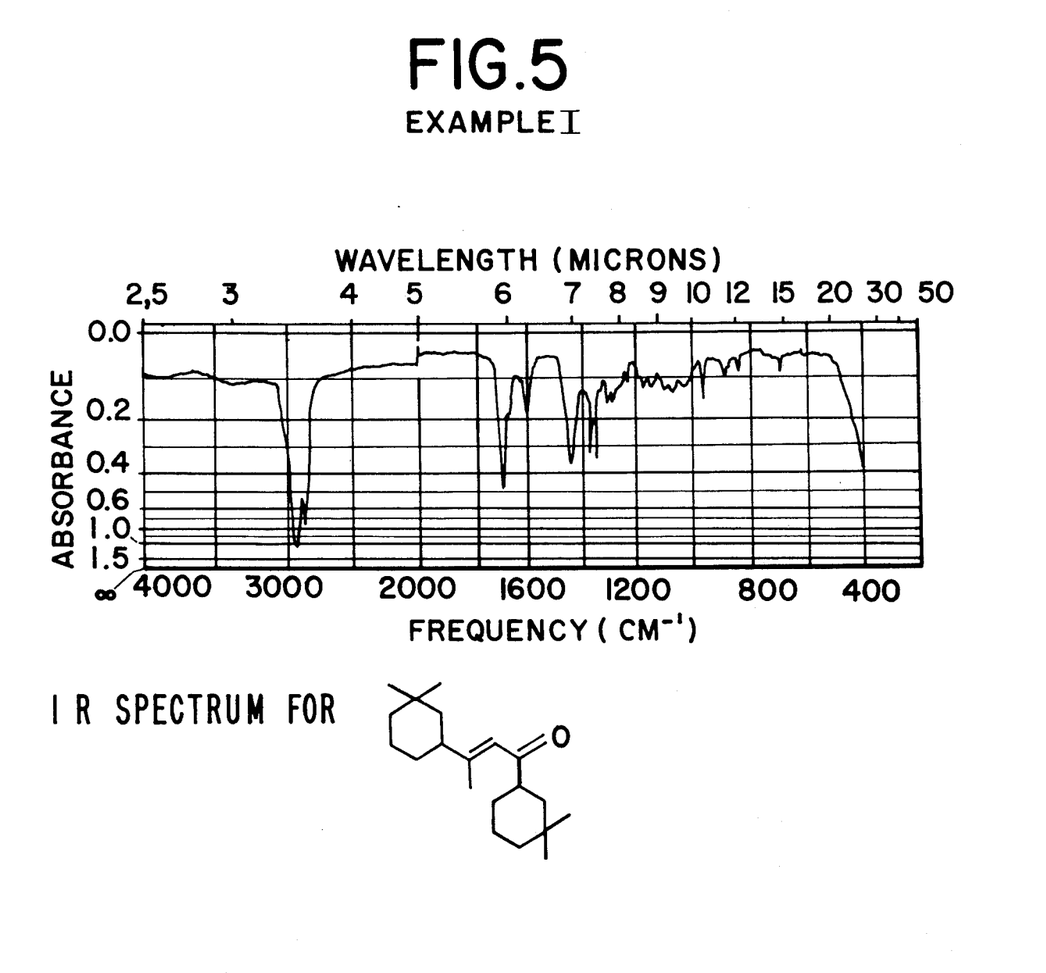

The Infrared analysis is as follows: 1600 cm$^{-1}$; C=C: 1700; C=O. The Mass Spectral analysis is as follows: m/e=111, 69, 55, 41, 43, 57, 290 (parent peak).

EXAMPLE II

A perfume composition is prepared by admixing the following ingredients in the indicated proportions:

| Ingredient | Amount (Grams) |
| --- | --- |
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamot Oil | 30 |
| Alpha Methyl Ionone | 25 |
| 1-Acetyl-3,3-dimethyl-(2-propenyl)cyclohexane produced according to the process of Example I | 10 |
| Cyclized Bicyclo C-12 material produced according to the process of Example IV of Canadian Patent 854,225, issued on October 20, 1970 | 5 |
| Isobornyl cyclohexyl alcohol | 10 |
| Benzyl Acetate | 25 |
| 2-n-Heptyl cyclopentanone | 5 |
| | 353.3 (TOTAL) |

The foregoing blend is evaluated and found to have a high degree of richness and persistence in its novel natural amber quality. This base composition can be admixed with aqueous ethanol, chilled and filtered to produce a finished cologne. The cologne so prepared has an amber aroma leaning towards a woody amber note. The base composition can also be used to scent soap or other toilet goods such as lotion, aerosol, sprays and the like.

EXAMPLE III

PREPARATION OF A COSMETIC POWDER COMPOSITION

A cosmetic powder is prepared by mixing in a ball mill, 100 g of talcum powder with 0.25 g of 1-acetyl-3,3-dimethyl(2-propenyl)cyclohexane produced according to Example I. It has an excellent woody, earthy, amber aroma.

EXAMPLE IV

PERFUMED LIQUID DETERGENT

Concentrated liquid detergents with woody, earthy and amber aromas (which detergents are produced from Lysine salt of n-dodecyl benzene sulfonic acid as more specifically described in U.S. Pat. No. 3,948,818, issued on Apr. 6, 1976) are prepared containing 1-acetyl-3,3-dimethyl-(2-propenyl) cyclohexane prepared according to Example I. They are prepared by adding and homogeneously mixing the appropriate quantity of 1-acetyl-3,3-dimethyl-(2-propenyl) cyclohexane in the liquid detergent. The detergents all possess a woody, earthy, amber aroma, the intensity increasing with greater concentrations of 1-acetyl-3,3-dimethyl-(2-propenyl) cyclohexane.

EXAMPLE V

PREPARATION OF A COLOGNE AND HANDKERCHIEF PERFUME

1-Acetyl-3,3-dimethyl-(2-propenyl)cyclohexane, prepared according to the process of Example I is incorporated in a cologne at a concentration of 2.5% in 85% aqueous ethanol; and into a handkerchief perfume at a concentration of 20% (in 95% aqueous ethanol). A distinct and definite woody, earthy, amber aroma is imparted to the cologne and to the handkerchief perfume.

EXAMPLE VI

PREPARATION OF A COLOGNE AND HANDKERCHIEF PERFUME

The composition of Example II is incorporated in a cologne at a concentration of 2.5% in 85% aqueous ethanol; and into a handkerchief perfume at a concentration of 20% (in 95% aqueous ethanol). The use of the 1-acetyl-3,3-dimethyl-(2-propenyl)cyclohexane in the composition of Example II affords a distinct and definite strong woody, earthy, amber aroma to the handkerchief perfume and cologne.

EXAMPLE VII

PREPARATION OF SOAP COMPOSITION

One hundred grams of soap chips are mixed with two grams of the composition of Example II until a substantially homogeneous composition is obtained. The perfumed soap composition manifests an excellent amber aroma with intense woody and earthy nuances.

EXAMPLE VIII

PREPARATION OF A DETERGENT COMPOSITION

A total of 100 grams of detergent (Lysine salt of n-dodecylbenzene sulfonic acid as more specifically described in U.S. Pat. No. 3,948,818, issued on Apr. 6, 1976) powder is mixed with 0.70 grams of the composition of Example II until a substantially homogeneous composition is obtained. This composition has an excellent amber aroma with intense earthy and sweet woody nuances.

EXAMPLE IX

RASPBERRY FLAVOR FORMULATION

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

1-Acetyl-3,3-dimethyl-(2-propenyl)cyclohexane is added to half of the above formulation at the rate of 2.0%. The formulation with the 1-acetyl-3,3-dimethyl-(2-propenyl)cyclohexane is compared with the formulation without the 1-acetyl-3,3-dimethyl-(2-propenyl)-cyclohexane at the rate of 0.01 percent (100 ppm) in water and evaluated by a bench panel.

The flavor containing the 1-acetyl-3,3-dimethyl-(2-propenyl)cyclohexane is found to have substantially sweeter aroma notes and a sweet raspberry, raspberry kernel-like and sweet aftertaste and mouthfeel missing in the basic raspberry formulation. It is the unanimous opinion of the bench panel that the chemical, 1-acetyl-3,3-dimethyl-(2-propenyl)cyclohexane rounds the flavor out and contributes to a very natural fresh aroma and taste as found in full ripe raspberries. Accordingly, the flavor with the addition of the 1-acetyl-3,3-dimethyl-(2-propenyl)cyclohexane is considered as substantially better than the flavor without 1-acetyl-3,3-dimethyl-(2-propenyl)cyclohexane.

EXAMPLE X

A. POWDER FLAVOR COMPOSITION

20 Grams of the flavor composition of Example IX is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F., and a wheel speed of 50,000 r.p.m.

B. SUSTAINED RELEASE FLAVOR

The following mixture is prepared:

| Ingredient | Parts by Weight |
|---|---|
| Liquid Raspberry Flavor Composition of Example IX | 20 |
| Propylene glycol | 9 |
| Cab-O-Sil ® M-5 (Brand of Silica produced by the Cabot Corporation of 125 High Street, Boston, Mass. 02110; Physical Properties: Surface Area: 200 m²/gm  Nominal particle size: 0.012 microns  Density: 2.3 lbs/cu.ft.) | 5.00 |

The Cab-O-Sil is dispersed in the liquid raspberry flavor composition of Example IX with vigorous stirring, thereby resulting in a viscous liquid. 71 Parts by weight of the powder flavor composition of Part A, supra, is then blended into the said viscous liquid, with stirring, at 25° C for a period of 30 minutes resulting in a dry, free flowing sustained release flavor powder.

EXAMPLE XI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example IX is added to the solution which is then homogenized to form an emulsion having particle size typically in the range of 2-5 microns. This material is kept at 120° F. under which conditions the gelatin will not jell.

Coascervation is induced by adding, slowly and uniformly 40 parts by weight of a 20% aqueous solution of sodium sulphate. During coascervation, the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XII

100 Parts by weight of chicle are mixed with 4 parts by weight of the flavor prepared in accordance with Example X. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE XIII

CHEWING GUM

100 Parts by weight of chicle are mixed with 18 parts by weight of the flavor prepared in accordance with Example XI. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE XIV

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example X |
| 100.00 (Total) | |

PROCEDURE:
1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1-1.5 minutes).

EXAMPLE XV

CHEWABLE VITAMIN TABLETS

The flavor material produced according to the process of Example XI is added to a Chewable Vitamin Tablet Formulation at a rate of 10 gm/kg which Chewable Vitamin Tablet Formulation is prepared as follows:

In a Hobart Mixer, the following materials are blended to homogeneity:

| | Gas/1000 tablets |
|---|---|
| Vitamin C (ascorbic acid) as ascorbic acid-sodium ascorbate mixture 1:1 | 70.0 |
| Vitamin $B_1$ (thiamine mononitrate) as Rocoat[R] thiamine mononitrate 33⅓% (Hoffman La Roche) | 4.0 |
| Vitamin $B_2$ (riboflavin) as Rocoat[R] riboflavin 33⅓% | 5.0 |
| Vitamin $B_6$ (pyridoxine hydrochloride) as Rocoat[R] pyridoxine hydrochloride 33⅓% | 4.0 |
| Niacinamide as Rocoat[R] niacinamide 33⅓% | 33.0 |
| Calcium pantothenate | 11.5 |
| Vitamin $B_{12}$ (cyanocobalamin) as Marck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example XXVIII | (as indicated above) |
| Sweetener - sodium saccharin | 1.0 |
| Magnesium stearate lubricant | 10.0 |
| Mannitol q.z. to make | 500.0 |

Preliminary tablets are prepared by slugging with flat-faced punches and grinding the slugs to 14 mesh. 13.5 Grams dry Vitamin A Acetate and 0.6 grams Vitamin D are then added as beadlets. The entire blend is then compressed using concave punches at 0.5 grams each.

Chewing of the resultant tablets yields a pleasant, long-lasting, consistently strong raspberry flavor for a period of 12 minutes.

What is claimed is:

1. The compound 1-acetyl-3,3-dimethyl-(2-propenyl) cyclohexane having the structure:

* * * * *